US005711957A

United States Patent [19]

Patat et al.

[11] Patent Number: 5,711,957
[45] Date of Patent: Jan. 27, 1998

[54] USE OF A POROUS CALCIUM CARBONATE BASED MATERIAL AS SUPPORT OF A GROWTH FACTOR IN THE PREPARATION OF A BIOABSORBABLE IMPLANT

[75] Inventors: Jean-Louis Patat; Jean-Pierre Ouhayoun, both of Paris, France

[73] Assignee: Inoteb, Saint-Gonnery, France

[21] Appl. No.: 360,801

[22] PCT Filed: May 11, 1994

[86] PCT No.: PCT/FR94/00565

§ 371 Date: Feb. 2, 1995

§ 102(e) Date: Feb. 2, 1995

[87] PCT Pub. No.: WO94/26322

PCT Pub. Date: Nov. 24, 1994

[30] Foreign Application Priority Data

May 13, 1993 [FR] France ................................ 93 05783
Nov. 17, 1993 [FR] France ................................ 93 13740

[51] Int. Cl.⁶ ........................................................ A61F 13/00
[52] U.S. Cl. ........................... 424/422; 424/423; 424/426; 424/428
[58] Field of Search ............................ 424/422, 423, 424/426, 428, 687

[56] References Cited

U.S. PATENT DOCUMENTS

| | | |
|---|---|---|
| 4,563,350 | 1/1986 | Nathan ........................... 424/95 |
| 4,917,702 | 4/1990 | Scheicher et al. ................ 623/16 |
| 5,240,710 | 8/1993 | Bar-Shalom et al. ............. 424/422 |
| 5,264,214 | 11/1993 | Rhee et al. ...................... 424/422 |

FOREIGN PATENT DOCUMENTS

| | | |
|---|---|---|
| 0 022 724 | 1/1981 | European Pat. Off. . |
| 0 395 187 A3 | 4/1990 | European Pat. Off. . |
| 0 395 187 | 10/1990 | European Pat. Off. . |
| 2 637 502 | 4/1990 | France . |
| 41 30 546 | 3/1993 | Germany . |
| 86/01726 | 3/1986 | WIPO . |
| 93/05823 | 4/1993 | WIPO . |

OTHER PUBLICATIONS

Damien, C. J. et al., "Bone Graft and Bone Graft Substitutes: A Review of Current Technology and Applications," *J. Applied Biomaterials*, vol. 2, 187–208 (1991).

*Journal of Cellular Biochemistry*, Supplement 15F, 1–7 Apr. 1991 Abstract CF15, ed. Wiley–Liss, P. Moullier et al. "Organoid Neovascular Structure: Effects of Various Matrix and Angiogenic Factors".

*Medicine Sciences*, vol. 9, No. 2, Feb. 1993, pp. 208–210, O. Danos "Reimplantation de cellules genetiquement modifiees dans des neo–organes vascularises," ed. John Libbey Eurotext.

Primary Examiner—Thurman K. Page
Assistant Examiner—Sharon Howard
Attorney, Agent, or Firm—Oliff & Berridge, P.L.C.

[57] ABSTRACT

A method for treating a living organism includes fitting in the living organism a bioabsorbable implant. The bioabsorbable implant includes a support of porous calcium carbonate based material for supporting at least one growth factor. The calcium carbonate based support material forms an external wall of the support.

24 Claims, No Drawings

USE OF A POROUS CALCIUM CARBONATE BASED MATERIAL AS SUPPORT OF A GROWTH FACTOR IN THE PREPARATION OF A BIOABSORBABLE IMPLANT

FIELD OF THE INVENTION

The subject of the invention is the use of a calcium carbonate based material as support for a growth factor in the preparation of a bioabsorbable implant intended to be fitted in a living organism.

Such a material can be used, in particular, as a bone-formation implant.

BACKGROUND

It is known that bone surgery often requires the fitting of bone grafts or implants constituting artificial replacements for such grafts.

Carrying out allografting raises objections, for obvious reasons of public health, in view of the risks of transmission of certain serious viral illnesses or illnesses caused by unconventional transmittable agents or "prions".

From this point of view, carrying out autografting is more satisfactory, but taking the graft leads to significant risks of morbidity; see, for example, Christopher J. Damien and J. Russell Parsons, Journal of Applied Biomaterials, Vol. 2, 187–208 (1991).

For these reasons, it has been recommended to use implants based on biocompatible materials such as tri-calcium phosphate, hydroxyapatite, plaster, coral, polymers based on poly(lactic acid) and/or poly(glycolic acid), etc.

Some of these materials, including calcium carbonate, are bioabsorbable and allow the progressive formation of newly formed bone tissue at the expense of the implanted material being absorbed; see especially European Patent 0,022,724.

It is moreover known that the presence of certain osteoinductive factors in the implants promotes bone regrowth. However, specialists have until now judged it to be necessary to add to the implant collagen acting as a support for the osteoinductive factors; see in this context the article by Damien and Russell Parsons already cited hereinabove and Patent Application FR-2,637,502.

SUMMARY OF THE INVENTION

It has now been discovered that a porous calcium carbonate based material such as coral can act as a support for osteoinductive factors, and more generally for growth factors, in the preparation of bioabsorbable implants and that the presence of collagen is neither necessary nor desirable in the case when the implant is intended to be used as a bone-formation implant.

DESCRIPTION OF PREFERRED EMBODIMENTS

The subject of the present invention is therefore the use of a porous calcium carbonate based material as support for at least one growth factor in the preparation of a bioabsorbable implant intended to be fitted in a living animal organism, in particular in a vertebrate, including humans, the said support being free of collagen in the case when the said growth factor is an osteoinductive factor.

When the growth factors are osteoinductive factors, the implants can be used as bone-formation implants. Of course, these implants may contain, in addition to the osteoinductive factors, other growth factors. The implants thus obtained can either be fitted as bone fillers which can be absorbed progressively in favour of newly formed tissue or implanted in a non-osseous site, for example connective tissue, where they give rise to bone tissue which can subsequently be used as a bone autograft material.

When the calcium carbonate support is loaded with a non-osteoinductive growth factor, it can be used in particular as a support for in vivo culture of living cells. Depending on the cells and the growth factors used, the implant, after fitting, may be used in particular as a support for obtaining tissue newly formed on the implantation site. This newly formed tissue can be used as a replacement for defective organ parts (pancreas/intestine connection, urethra, bladder, pericardium, etc.).

The implant of the invention can also be used as an in vivo culture support for cells which have been genetically modified, especially by insertion of a suitable gene, in a manner which is known per se, in order to remedy a genetic defect. The modified cells may also come from autologous sampling. The implants thus obtained constitute an "organoid" serving as a therapeutic treatment device, fitting of which makes it possible to make up for a defective organ, and in particular to remedy certain dysfunctions of genetic origin. This is therefore a novel way of implementing genetic therapies.

For example, a hollow coral piece may be made, provided with an opening which can be closed off by a screwed or press-fitted plug which is also made of coral. For example, for implantation in humans, this may be a hollow cylinder having a height of from 2 to 10 cm, an external diameter of from 1 to 3 cm and an internal diameter of from 0.5 to 2 cm. The internal wall may be impregnated with a collagen loaded with growth factors such as TGF-beta. The external wall may be impregnated with a solution of an angiogenic factor (FGF). The modified autologous cells (for example fibroblasts) are previously cultivated in vitro on a solid support such as a network of collagen fibres or coral granules. The culture of modified cells is introduced, with its solid support, into the hollow part of the implant. The latter is then closed off using the plug and the implantation, for example intra-abdonimal, is carried out. The implanted cells become organized into a vascularized tissue surrounded by a connective tissue replacing the coral as it is resorbed.

The cells introduced into the implant may be undifferentiated cells, the differentiation of which is carried out using endogenous or exogenous cytokines.

The calcium carbonate based material usable as a support for growth factors is preferably aragonite. Use may, in particular, be made of coral skeleton. One of the advantages of using coral skeleton is that it contains communicating pores which promotes neovascularization as well as invasion of the material by bone cells or other cells previously introduced or recruited in situ.

A material having pore diameters lying between 50 and 500 microns, in particular between 200 and 400 microns, is preferably used as support material. The porosity, that is to say the proportion by volume of the pores as a ratio of the total volume of the material generally lies between 20 and 80%, for example between 40 and 60%.

Materials of this type can be obtained by using, in particular, coral of the genera Porites, Acropora, Goniopora, Lobophyllia, Simphyllia and Millipora.

It is known that growth factors are polypeptides which act locally on certain cells and influence their proliferation, their migration and/or their differentiation or which stimulate the production of other growth factors.

Numerous growth factors are currently known.

For example, growth factors having an osteoinductive effect are known and their effects have been studied, in particular in vitro, on cultures of various bone cells.

Among growth factors whose activity is specific to the osseous medium, mention may be made of certain proteins of demineralized bone, or DBM (Demineralized Bone Matrix) and in particular the proteins called BP (Bone Protein) or BMP (Bone Morphogenetic Protein) which actually contain a plurality of constituents; in humans, for example, the constituents called osteonectin and osteocalcin have, in particular, been isolated. Another active protein is osteogenin.

Among the growth factors influencing cellular growth in general, including the growth of bone cells, mention may in particular be made of somatomedins or IGF (Insulin-like Growth Factor), PDGF (Platelet-Derived Growth Factor), FGF (Fibroblast Growth Factor), BDGF II (or beta-2-microglobulin), TGFs (Transforming Growth Factor), in particular TGF-beta (or bTGF) etc.

The usable doses of growth factors are known or can be determined by routine experiments on animal models. Use is generally made of growth factors whose action is local, at doses of a few micrograms or of a few tens of micrograms.

The invention also relates to the preparation of porous calcium carbonate supports loaded with growth factors. The latter can be incorporated

- by impregnation, optionally followed by drying, using a solution or a gel containing the growth factor,
- by deposition of films by capillary action using a solution of the growth factor by binding with the calcium carbonate by means of a coating with electronegative surface potential (heparin, heparan sulphate, dextrane sulphate, dermatane sulphate, xylane sulphate, etc.).

It is possible to facilitate fixing and retention of the growth factors on the calcium carbonate support by applying them in the form of a combination with a binder, especially a binder capable of forming a gel. Such binders are known. They are, for example, collagen or cellulose derivatives such as methylcellulose, hydroxypropylcellulose, hydroxypropylmethylcellulose, carboxymethylcellulose, etc. These products are biocompatible. They are commercially available. Use may also be made, as binders, of a fibrin precursor, for example fibrinogen or a biological adhesive (cryoprecipitate).

The binder has, in particular, the effect of promoting fixing of the growth factor and optionally its progressive release.

The binder is generally progressively absorbed as the implant is reincorporated by a newly formed tissue.

It has, however, been observed that, in the case of a bone-formation implant, the presence of collagen as binder does not promote the creation of new bone tissue but would, however, tend to retard it.

The following examples illustrate the invention.

EXAMPLE 1

Coral discs having a diameter of 6 mm and a thickness of 2 mm (origin: INOTEB) is used as starting material.

A bovine BP having a protein concentration of 1.52 mg/ml is used as osteoinductive factor.

The BP is diluted so as to obtain doses of 10, 35 and 100 micrograms of active principle in a volume of 20 microliters. Each coral disc is impregnated with 20 microliters of one of the solutions obtained. After infiltration of the solution into the pores, the discs are frozen rapidly then subjected to freeze-drying.

With the discs thus treated, subcutaneous implants are made in the ventral region in rats. Use is made of three groups of five animals which each receive a coral implant impregnated with 10, 35 or 100 micrograms of BP, respectively.

After 27 days, a dose of 20 mg/kg of a labelling agent consisting of calcein is administered subcutaneously to the animals. On the twenty-eighth day, the implants are extracted, weighed, photographed and fixed in methanol. The samples are coated in poly(methyl methacrylate) with a view to histological examination. The samples are sectioned and coloured with the reagent Rapid Bone Stain and with Van Gieson's picro-fuchsin. The sections are examined under a microscope.

The weights of the coral discs before implantation and after explantation are indicated in Table 1 below, in which the results are expressed in the form of a mean ± standard deviation.

TABLE 1

| | Weight of the discs (mg) | | |
|---|---|---|---|
| Group | before implantation | after explantation | weight gain |
| I | 86.0 ± 11.2 | 97.2 ± 13.0 | 11.2 ± 6.0 |
| II | 84.4 ± 4.1 | 114.2 ± 14.2 | 29.8 ± 12.1 |
| III | 83.2 ± 9.5 | 128 ± 12.2 | 45.4 ± 10.1 |

In group I, examination under a microscope shows a formation of bone which is still immature and haematopoietic marrow throughout the implant, as well as the formation of bone at the surface. The bone forms and conduction by the material allows growth of the bone. There is a balance between osteoinduction and osteoconduction.

In group II, mineralization is good throughout the implant, the newly formed bone is mature and covers the coral. Osteoinduction predominates over osteoconduction and there is more bone on the periphery of the implant.

In group III, the samples have a thick outer edge of mature bone with haematopoietic marrow at the center. In several cases, cartilage and cartilage undergoing mineralization are observed after a few weeks.

EXAMPLE 2

Trephination is carried out on rats by removal of a circular button with a diameter of 8 mm from the top of the cranium. A coral disc having a diameter of 8 mm is applied into the window thus obtained. The coral discs are impregnated in a manner similar to that described in the preceding example, by the osteoinductive factor (recombinant human BMP-2), in a ratio of 0.5 microgram of BMP-2 to 1 mg of coral. On the day of the operation, calcein is injected intramuscularly in a proportion of 20 mg/kg. On the twenty-seventh day, xylenol orange (90 mg/kg) is injected intramuscularly.

These dyes give a yellow and orange fluorescence outlining the bone formations.

On the twenty-eighth day, a part of the top of the cranium including the implant is sampled and it is fixed in neutral 10% aqueous formaldehyde solution for histological study after inclusion in methyl methacrylate on non-demineralized sections dyed with the dye Giemsa-Paragon. Microradiographs demonstrate mineralization.

The sections show a bone formation starting from the borders of the bone lesion and extending over the edges of the coral disc.

In the case of the coral impregnated with BPM-2, bone is present over the entire disc. Absorption of the coral is more rapid than in the absence of BMP-2.

EXAMPLE 3

Bilateral and symmetrical trephination of the cranium is carried out on rabbits at the level of the parietal bones, by removal of two circular buttons with a diameter of 10 mm.

Five batches of rabbits are taken: four test groups and one control group. A single side is treated in the individuals of each test group.

Group 1 (symbol MF): 50 microliters of methylcellulose gel containing 1 µg of TGF-beta is applied into one of the windows.

Group 2 (symbol BF): 100 µl of biological adhesive to which one 1 µg of TGF-beta was added is applied into one of the windows.

Group 3 (symbol BCF): 50 microliters of a mixture similar to that applied to the BF group, but additionally containing 70 mg of Porites coral granulates marketed under the name BIOCORAL 450 by the Company INOTEB is applied.

Group 4 (symbol BC): the same mixture as for group 3 was applied, but without growth factor.

The evolution of bone construction is followed by cranial tomodensitometry. The diameters and areas of the trephinations are measured on an image analyser. After sacrifice of the animals studied, after one month, the top of the cranium is sampled then prepared with a microtome for histological analysis by histomorphometry and fluorescence microscopy. In order to label the bone formation surfaces, 2 ml of oxytetraquinol were injected on the tenth and third days preceding sacrifice.

The following observations were made:

After 30 days, groups BC and BCF have completely covered the scar with an osteoid tissue.

For the other groups, covering is not complete. The diameter on the treated side is less than the diameter on the control side. The diameter on the control side is less than the diameters observed in the control group.

The bone span volume (BSV) was determined by histomorphometry.

The BCF group has the highest BSV, followed by the BC group.

Studying the animals in the groups treated with coral shows that the granulates are absorbed progressively. Coral allowed the rapid creation of bone spans between these granulates.

In general, the addition of the growth factor increases the remineralization rate.

EXAMPLE 4

A piece of coral (porosity: 50%) is covered with a mouse collagen gel of type I containing an angiogenic growth factor (bFGF).

By using a bFGF labelled with radioactive iodine it was possible to show, by release tests, that the binding of the bFGF to the coral support is very strong. This binding is further enhanced in the presence of heparans or heparins.

The pieces of coral thus treated are implanted subcutaneously in mice. Macroscopic and histological observation of the implants is carried out for one year.

In a few months the coral is absorbed. It is replaced by connective tissue of the same size and the same shape as the implant. At the end of three months strong vascularization and the absence of any inflammatory cell next to the coral residues is observed. The connective tissue is formed by mesenchymal cells of low density.

In other experiments, the collagen was replaced by carboxymethylcellulose or fibrinogen.

EXAMPLE 5

A hollow coral cylinder is made.

A network of collagen fibres containing autologous fibroblasts genetically modified by insertion of a gene using a retroviral vector is introduced into the hollow part.

The external wall of the cylinder was previously impregnated with a collagen gel of type I associated with heparin. The coral thus pretreated is incubated in the presence of an angiogenic growth factor (bFGF). Finally, the cylinder is closed off using a coral plug and intraperitoneal implantation is carried out in a dog of mass 25 kg.

After 45 days the implant is withdrawn. The vascularization of the latter is significant and comprises vessels of large calibre. Absorption of the coral is initiated. The modified cells are viable and express the inserted gene.

They are organized into a vascularized tissue.

A similar experiment was carried out on mice deficient in beta-glucuronidase and having a lysosomal accumulation disease. A human cDNA coding for beta-glucuronidase is inserted into a retroviral vector which is subsequently used for modifying (autologous) mouse cells. The modified cells are introduced into a network of collagen fibres and the whole is introduced into a coral cylinder treated in a manner similar to that described hereinabove. The implants thus prepared are inserted into the mesentery of the deficient mice.

The implanted modified cells are capable of secreting the missing enzyme which passes into the general circulation, thus leading to remission of the physiological consequences of the genetic defect, and in particular the correction of the hepatic and splenic lesions.

We claim:

1. A method of treating a living organism comprising fitting in said living organism a bioabsorbable implant having a support of porous calcium carbonate based material supporting at least one growth factor, said support being free of collagen in a case when said growth factor is an osteoinductive factor and wherein said calcium carbonate based material comprises an external wall.

2. A method according to claim 1, wherein said porous calcium carbonate is in the form of aragonite.

3. A method according to claim 1, wherein said growth factor is an osteoinductive factor.

4. A method according to claim 3, wherein said bioabsorbable implant is fitted as a bone filler.

5. A method according to claim 3, wherein said bioabsorbable implant is fitted in a non-osseous site.

6. A method according to claim 1, wherein said growth factor is a non-osteoinductive factor.

7. A method according to claim 6, wherein said bioabsorbable implant supports an in vivo cell culture.

8. A method according to claim 7, wherein said bioabsorbable implant is in the form of a hollow piece provided with an opening which can be closed off by a plug.

9. A method according to claim 8, wherein said at least one growth factor is deposited by impregnation on an internal wall of said hollow piece.

10. A method according to claim 8, wherein a cell culture to be cultivated is introduced into a hollow part of said bioabsorbable implant and said hollow part is then closed off using said plug before carrying out implantation.

11. A method according to claim 1, wherein said living organism is a vertebrate.

12. A method according to claim 2, wherein said porous calcium carbonate is in the form of coral skeleton.

13. A method of preparing a bioabsorbable implant having a porous calcium carbonate support as a support for at least one non-osteoinductive growth factor, comprising forming a porous calcium carbonate support and applying on said calcium carbonate support a solution or a gel containing said at least one non-osteoinductive growth factor.

14. A method according to claim 13, wherein said solution or gel is applied by impregnation or deposition.

15. A method according to claim 14, wherein said deposition comprises binding said solution to said support by coating said support with a film having electronegative surface potential.

16. A method according to claim 15, wherein said film comprises heparin, heparan, sulphate, dextrane sulphate, dermatane sulphate or xylane sulphate.

17. A bioabsorbable implant to be fitted in a living organism, comprising a support including a porous calcium carbonate based material and at least one growth factor, said calcium carbonate support containing said at least one growth factor and having an unmodified surface.

18. A method of treating a living organism comprising fitting in said living organism a bioabsorbable implant having a support consisting essentially of a porous calcium carbonate based material supporting at least one growth factor, said support being free of collagen in a case when said growth factor is an osteoinductive factor.

19. A bioabsorbable implant to be fitted in a living organism, comprising a support consisting essentially of a porous calcium carbonate based material and at least one growth factor, said calcium carbonate support containing said at least one growth factor.

20. The method of claim 18, wherein said calcium carbonate is in the form of aragonite.

21. The method of claim 18, wherein said growth factor is an osteoinductive factor.

22. The method of claim 21, wherein said implant is fitted as a bone filler.

23. The method of claim 21, wherein said implant is fitted in a non-osseous site.

24. The method of claim 18, wherein said growth factor is a non-osteoinductive factor.

* * * * *